United States Patent [19]

Badger et al.

[11] Patent Number: 5,786,376
[45] Date of Patent: Jul. 28, 1998

[54] METHODS OF TREATING OPPORTUNISTIC INFECTIONS WITH AZASPIRANES

[75] Inventors: Alison Mary Badger, Bryn Mawr; Peter John Bugelski, Philadelphia; Danuta J. Herzyk, Valley Forge, all of Pa.

[73] Assignee: SmithKline Beecham Corporation, Philadelphia, Pa.

[21] Appl. No.: 507,487

[22] PCT Filed: Jul. 14, 1995

[86] PCT No.: PCT/US95/08915

§ 371 Date: Jan. 21, 1997

§ 102(e) Date: Jan. 21, 1997

[87] PCT Pub. No.: WO96/03126

PCT Pub. Date: Feb. 8, 1996

[30] Foreign Application Priority Data

Jul. 23, 1994 [GB] United Kingdom ............... 9414902

[51] Int. Cl.$^6$ ............... A61K 31/40; A61K 31/44; A61K 31/55
[52] U.S. Cl. ............... 514/409; 514/278; 514/212
[58] Field of Search ............... 514/278, 409, 514/212

[56] References Cited

U.S. PATENT DOCUMENTS 4,963,557  10/1990  Badger et al. ............... 514/278

Primary Examiner—Jerome D. Goldberg
Attorney, Agent, or Firm—Cushman Darby & Cushman IP Group Pillsbury Madison & Sutro LLP

[57] ABSTRACT

Invented is a method of treating opportunistic infections in a mammal, including a human, in need thereof which comprises administering to such mammal an effective amount of a substituted azaspirane.

6 Claims, 2 Drawing Sheets

EFFECT OF COMPOUND (A) ON CANDIDACIDAL ACTIVITY OF RAT ALVEOLAR MACROPHAGES

*Significantly greater than control $P<0.001$

METHODS OF TREATING OPPORTUNISTIC INFECTIONS WITH AZASPIRANES

METHODS

This invention relates to a method of treating opportunistic infections in a mammal, including a human, in need thereof which comprises administering to such mammal an effective amount of a substituted azaspirane.

BACKGROUND OF THE INVENTION

Opportunistic infections are an increasing problem in medicine. Opportunistic infections can be caused by a wide variety of bacteria, viruses, fungi and protozoa, as described in *Microbiology* 16th edition. Appleton Crofts, N.Y., 1976, p 405. Of particular interest are e.g. *Candida sp., Pseudomonas sp., Listeria sp., Pneumocystis carinii, Pneumococci, Neisseria sp., Salmonella sp., Mycobacteria sp., Cryptococcus sp., Aspergillis sp., Cryptosporidium sp., Herpes simplex, Herpes zoster, Cytomegalovirus* and *Toxoplasma sp.* These organisms, which are often part of the normal flora, are rarely a cause for concern in normal hosts but, under certain circumstances, can cause serious disease. These circumstances include but are not limited to: prolonged high dose antibiotic therapy, cancer chemotherapy, transplantation and acquired immunodeficiency syndrome (AIDS). In the first two examples cited, a Biologic Response Modifier, (i.e., compounds with immunostimulatory activity, e.g. muramylpeptides) would be the adjunct treatment of choice for an opportunistic infection (Walsh TH et al. *Curr Opin Oncol* 4:647–655, 1992). In the latter two examples, however, immunostimulation may be contraindicated. In the case of transplantation, a Biologic Response Modifier would be expected to exacerbate graft rejection of graft versus host disease. In AIDS, simple immunostimulation may accelerate disease progression.

Immunomodulatory agents are, in general, not known for their ability to treat opportunistic infections. Further, there is presently no acceptable means for predicting whether a particular class of immunomodulatory agents will have utility in treating opportunistic infections.

Badger, et al., U.S. Pat. No. 4,963,557 (Badger I) discloses compounds of the formula I:

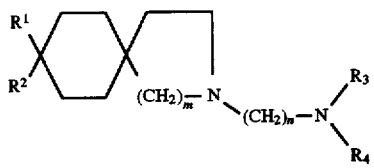

wherein: n is 3–7; m is 1 or 2; $R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms; $R^3$ and $R^4$ are the same or different and are selected from hydrogen or straight chain alkyl having 1–3 carbon atoms; or $R^3$ and $R^4$ are joined together with the nitrogen atom to form a heterocyclic group having 5–8 atoms; or a pharmaceutically acceptable salt or hydrate or solvate thereof.

Badger I discloses compounds of Formula I as a class of novel compounds which induce an immunomodulatory effect which is characterized by the stimulation of suppressor cell activity.

Badger I does not disclose the compounds of Formula I as agents for treating opportunistic infections.

SUMMARY OF THE INVENTION

This invention relates to a method of treating opportunistic infections in a mammal, including a human, in need thereof which comprises administering to such mammal an effective amount of a compound of the formula

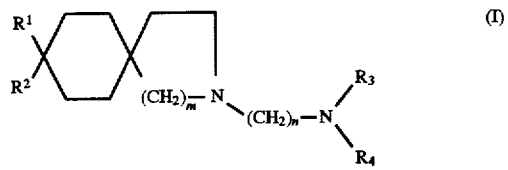

wherein:

n is 3–7;

m is 1 or 2;

$R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms;

$R^3$ and $R^4$ are the same or different and are selected from hydrogen or straight chain alkyl having 1–3 carbon atoms; or $R^3$ and $R^4$ are joined together with the nitrogen atom to form a heterocyclic group having 5–8 atoms; or a pharmaceutically acceptable salt or hydrate or solvate thereof.

DETAILED DESCRIPTION OF THE INVENTION

Figure 1:
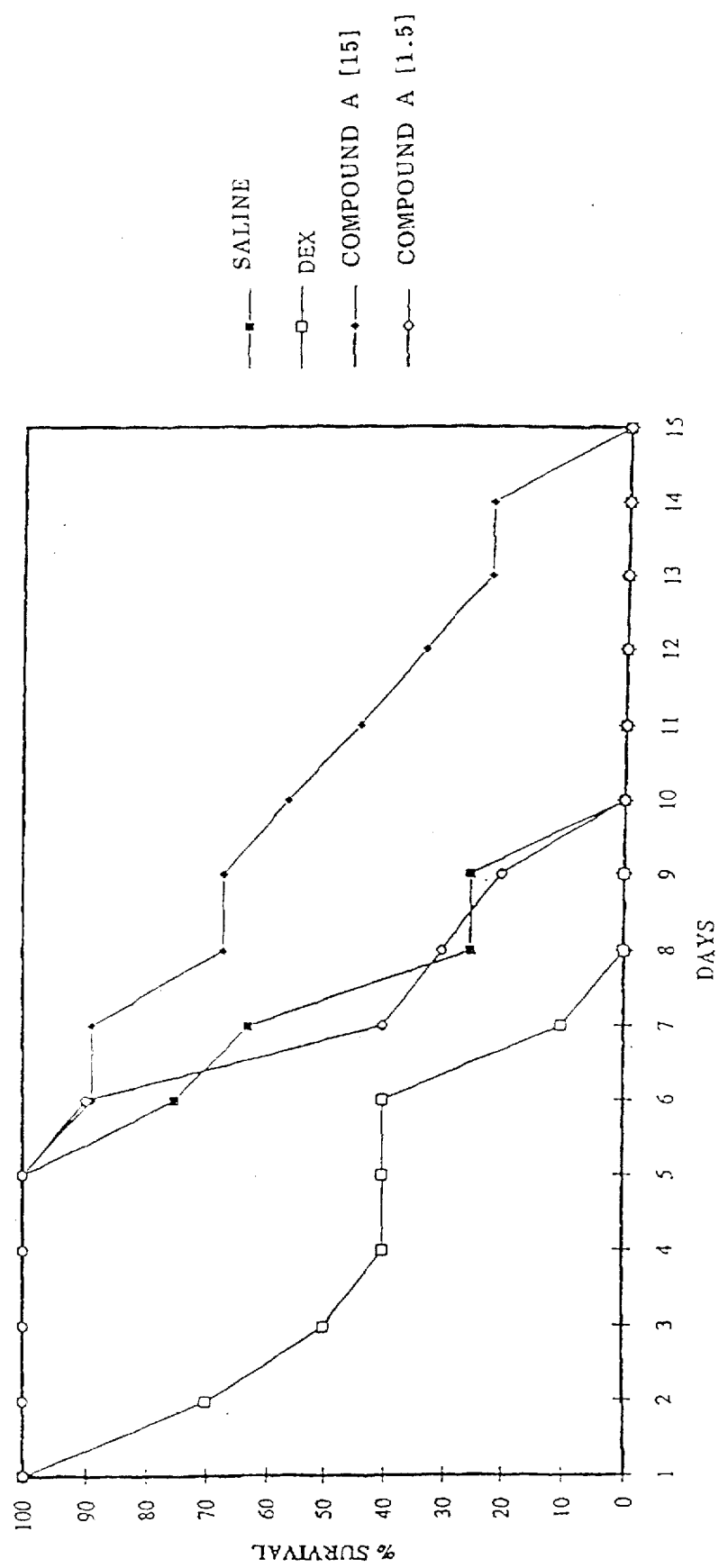
Figure 2:
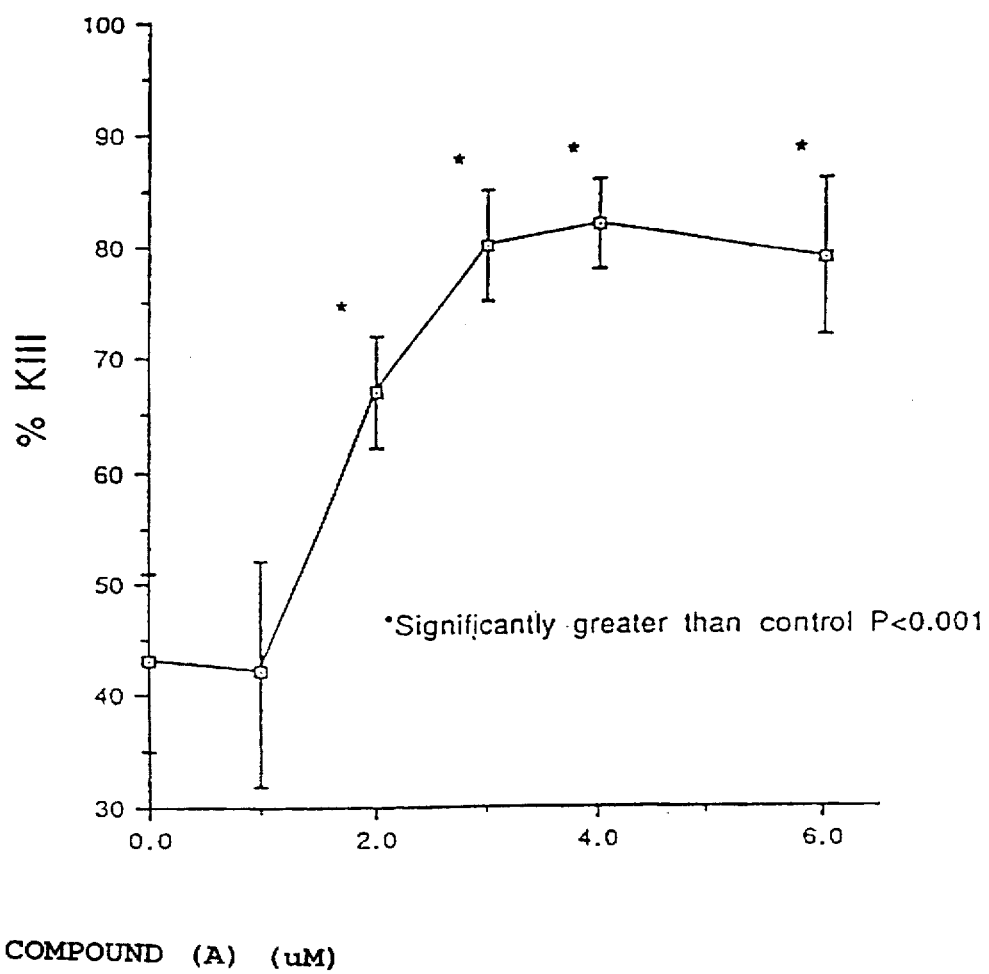

The preparation of all compounds of Formula (I) and pharmaceutically acceptable salts, hydrates and solvates and formulations thereof is disclosed in U.S. Pat. No. 4,963,557, the entire disclosure of which is hereby incorporated by reference.

A preferred compound used in the novel method is the dihydrochloride salt of a compound of Formula (I) where $R^1$ and $R^2$ are propyl, $R^3$ and $R^4$ are methyl, m is 1 and n is 3 which is N,N-dimethyl-8,8-dipropyl-2-azaspiro[4.5]decane-2-propanamine dihydrochloride.

A particularly preferred compound used in the novel method is the dihydrochloride salt of a compound of Formula (I) where $R^1$ and $R^2$ are propyl, $R^3$ and $R^4$ are ethyl, m is 1 and n is 3 which is N,N-diethyl-8,8-dipropyl-2-azaspiro[4.5]decane-2-propanamine dihydrochloride.

A particularly preferred compound used in the novel method is the dihydrochloride salt of a compound of Formula (I) where $R^1$ and $R^2$ are propyl, $R^3$ and $R^4$ are joined together with the nitrogen to form a piperidine ring, m is 1 and n is 3 which is 8,8-dipropyl-2-azaspiro[4.5]decane-2-piperidinopropyl dihydrochloride.

As used herein, the term "compound A" refers to the dihydrochloride salt of a compound of Formula (I) where R1 and R2 are propyl, R3 and R4 are methyl, m is 1 and n is 3 which is N,N-dimethyl-8,8-dipropyl-2-azaspiro[4.5]decane-2-propanamine dihydrochloride.

It has now been discovered that compounds of Formula (I) and pharmaceutically acceptable salts or hydrates or solvates thereof are useful for treating opportunistic infections in a mammal, including a human, in need thereof. By the term "treating" is meant prophylactic or therapeutic therapy.

Compound A was tested for its in vivo ability to treat opportunistic infections in Experiment 1. To perform Experiment 1 Compound A was dissolved in saline and administered to CBA/J mice, at 0, 1.5, or 15 mg/kg, by daily intraperitoneal injection for 14 days. Control mice received saline. On day 8, all mice received an intravenous injection of $1\times10^6$ *Candida Albicans* (Strain B311). Survival was monitored daily until all mice died or were sacrificed for humane reasons. There was a significant increase in the mean survival time in the mice that received 15 mg/kg. In contrast, mice that received intraperitoneal 5 doses of dexamethasone (an immunosuppressive steriod) at 50 mg/kg showed a significant decrease in mean survival time.

Compound A was tested in an ex vivo experiment (Experiment 2) for its ability to treat opportunistic infections. In Experiment 2 Lewis rats received oral doses of 20 mg/kg of Compound A dissolved in 0.5% Tragacanth (5 doses/wk) for 16 days. On day 23 the rats were sacrificed and alveolar macrophages were collected by brochoalveolar lavage. The cells were dispensed into 24 well dishes and their ability to kill *Candida albicans* evaluated. There was a significant increase in the ability of cells from rats treated with Compound A to kill two strains (B311 and B792) of *candida*.

Compound A was tested in an in vitro experiment (Experiment 3) for its ability to treat opportunistic infections. In Experiment 3 alveolar macrophges were collected by lavage from untreated rats and were incubated with Compound A in vitro for 3 days. At that time, the compound was washed off and the cells ability to kill *Candida albicans* (Strain B792) was evaluated. There was a statistically significant concentration dependent increase in kill percentage at $\geq 2$ uM Compound A. This effect is not due to a direct effect of Compound A on the growth of *Candida albicans as concentrations up to* 12 uM had no effect on the yeast.

This invention relates to a method of treating opportunistic infections in a mammal, including a human, in need thereof which comprises administering to such mammal an effective amount of a compound of Formula (I) or a pharmaceutically acceptable salt or hydrate or solvate thereof. A compound of Formula (I) or a pharmaceutically acceptable salt or hydrate or solvate thereof can be administered to such mammal including a human, in a conventional dosage form prepared by combining a compound of Formula (I) or a pharmaceutically acceptable salt or hydrate or solvate thereof, with a conventional pharmaceutically acceptable carrier or diluent according to known techniques, such as those described in Badger (I), U.S. Pat. No. 4,963,557.

It will be recognized by one of skill in the art that the form and character of the pharmaceutically acceptable carrier or diluent is dictated by the amount of active ingredient with which it is to be combined, the route of administration and other well-known variables. A compound of Formula (I) or a pharmaceutically acceptable salt or hydrate or solvate thereof is administered to a mammal, including a human in an amount sufficient to treat opportunistic infections.

The route of administration of the Formula (I) ("active ingredient") compound is not critical but is usually oral or parenteral, preferably oral.

The term parenteral as used herein includes intravenous, intramuscular, subcutaneous, intranasal, intrarectal, transdermal, intravaginal or intraperitoneal administration. The subcutaneous and intramuscular forms of parenteral administration are generally preferred. The daily parenteral dosage regimen will preferably be from about 0.01 mg/kg to about 10 mg/kg of total body weight, most preferably from about 0.1 mg/kg to about 1 mg/kg. Preferably, each parenteral dosage unit will contain the active ingredient in an amount of from about 0.1 mg to about 100 mg.

The compounds of Formula (I) which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavoring or coloring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

The daily oral dosage regimen will preferably be from about 0.01 mg/kg to about 10 mg/kg of total body weight. Preferably each oral dosage unit will contain the active ingredient in an amount of from about 0.1 mg to about 100 mg.

While it is possible for an active ingredient to be administered alone, it is preferable to present it as a pharmaceutical formulation.

It will be recognized by one of skill in the art that the optimal quantity and spacing of individual dosages of a compound of formula (I) or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt or hydrate or solvate thereof given per day and duration of therapy, can be ascertained by those skilled in the art using conventional course of treatment determination tests.

The method of this invention of treating opportunistic infections in a mammal, including a human, comprises administering to a subject in need of such treatment an effective amount of a pharmaceutically active compound of the present invention.

The invention also provides for the use of a compound of Formula (I) in the manufacture of a medicament for use in the treatment of opportunistic infections in a mammal, including a human.

The invention also provides for a pharmaceutical composition for use in the treatment of opportunistic infections in a mammal, including a human.

The invention also provides for a process for preparing a pharmaceutical composition containing a pharmaceutically acceptable carrier or diluent and a compound of Formula I which comprises bringing the compound of Formula I into association with the pharmaceutically acceptable carrier of diluent.

No unacceptable toxicological effects are expected when compounds of the invention are administered in accordance with the present invention.

Following are the results of testing the compounds of this invention.

Table I

The effect of N,N-dimethyl-8,8-dipropyl-2-azaspiro[4.5] decane-2-propanamine dihydrochloride (Compound A) on treating opportunistic infections ex vivo from Experiment 2.

TABLE 1

Effect of Candidacidal Activity of Rat Bronchoalveolar Cells

| TREATMENT | STRAIN OF CANDIDA | OPSONIZATION | % Kill ± S.D. |
|---|---|---|---|
| Control | B311 | none | 31 ± 12 |
| Control | B311 | 2% rat serum | 56 ± 6 |
| 20 mg/kg | B311 | none | 67 ± 9* |
| 20 mg/kg | B311 | 2% rat serum | 84 ± 6* |
| Control | B792 | none | 36 ± 4 |
| Control | B792 | 2% rat serum | 79 ± 6 |
| 20 mg/kg | B792 | none | 71 ± 11* |
| 20 mg/kg | B792 | 2% rat serum | 94 ± 1* |

*Significantly greater than control, P < 0.001

The data in the above table, from in vivo, ex vivo and in vitro experiments, demonstrates the unexpected therapeutic effect of compounds of Formula I on treating opportunistic infections.

In addition, the compounds of the present invention can be co-administered with further active ingredients, such as compounds known to treat opportunistic infections.

Without further elaboration, it is believed that one skilled in the art can, using the preceding description, utilize the present invention to its fullest extent. The following examples are, therefore, to be construed as merely illustrative and not a limitation of the scope of the present invention in any way.

EXAMPLE 1—CAPSULE COMPOSITION

An oral dosage form for administering Formula (I) compounds is produced by filing a standard two piece hard gelatin capsule with the ingredients in the proportions shown in Table II, below.

TABLE II

| INGREDIENTS | AMOUNTS |
|---|---|
| N,N-diethyl-8,8-dipropyl-2-azaspiro[4,5]decane-2-propanamine dihydrochloride | 25 mg |
| Lactose | 55 mg |
| Talc | 16 mg |
| Magnesium stearate | 4 mg |

EXAMPLE 2—INJECTABLE PARENTERAL COMPOSITION

An injectable form for administering Formula (I) compounds is produced by stirring 1.5% by weight of N,N-diethyl-8,8-dipropyl-2-azaspiro[4,5]decane-2-propanamine dihydrochloride in 10% by volume propylene glycol in water.

EXAMPLE 3—TABLET COMPOSITION

The sucrose, calcium sulfate dihydrate and Formula (I) compound shown in Table III below, are mixed and granulated in the proportions shown with a 10% gelatin solution. The wet granules are screened, dried, mixed with the starch, talc and stearic acid, screened and compressed into a tablet.

TABLE III

| Ingredients | Amounts |
|---|---|
| N,N-diethyl-8,8-dipropyl-2-azaspiro[4,5]decane-2-propanamine dihydrochloride | 20 mg |
| calcium sulfate dihydrate | 30 mg |
| sucrose | 4 mg |
| starch | 2 mg |
| talc | 1 mg |
| stearic acid | 0.5 mg |

While the above descriptions and examples fully describe the invention and the preferred embodiments thereof, it is understood that the invention is not limited to the particular disclosed embodiments coming within the scope of the following claims.

What is claimed is:

1. A method for treating opportunistic infections caused by an organism selected from the group consisting of *Candida sp., Pseudomonas sp., Listeria sp., Pneumocystis carinii, Pneumococci, Neisseria sp., Salmonella sp., Mycobacteria sp., Cryptococcus sp., Aspergillis sp., Cryptosporidium sp., Herpes simplex, Herpes zoster, Cytomegalovirus* and *Toxoplasma sp.* in a mammal including a human subject to such infection which comprises administering to said human an effective amount of a compound of the formula $$R^1 \diagdown \diagup \diagdown \diagup \diagdown \diagup R_3$$
$$R^2 \diagup \diagdown \diagup \diagdown (CH_2)_m - N \diagdown (CH_2)_n - N \diagup R_4 \quad (I)$$

wherein:

n is 3–7;

m is 1 or 2;

$R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms;

$R^3$ and $R^4$ are the same or different and are selected from hydrogen or straight chain alkyl having 1–3 carbon atoms; or $R^3$ and $R^4$ are joined together to form a cyclic alkyl group having 4–7 atoms; or a pharmaceutically acceptable salt or hydrate or solvate thereof.

2. The method of claim 1 wherein the compound is N,N-diethyl-8,8-dipropyl-2-azaspiro[4.5]decane-2-propanamine; or a pharmaceutically acceptable salt, hydrate or solvate thereof.

3. The method of claim 1 wherein the compound is administered orally.

4. The method of claim 3 wherein from about 0.01 mg/kg to about 10 mg/kg of compound is administered per day.

5. The method of claim 1 wherein the compound is administered parenterally.

6. The method of claim 5 wherein from about 0.01 mg/kg to about 10 mg/kg of compound is administered per day.

* * * * *